Figure 1:
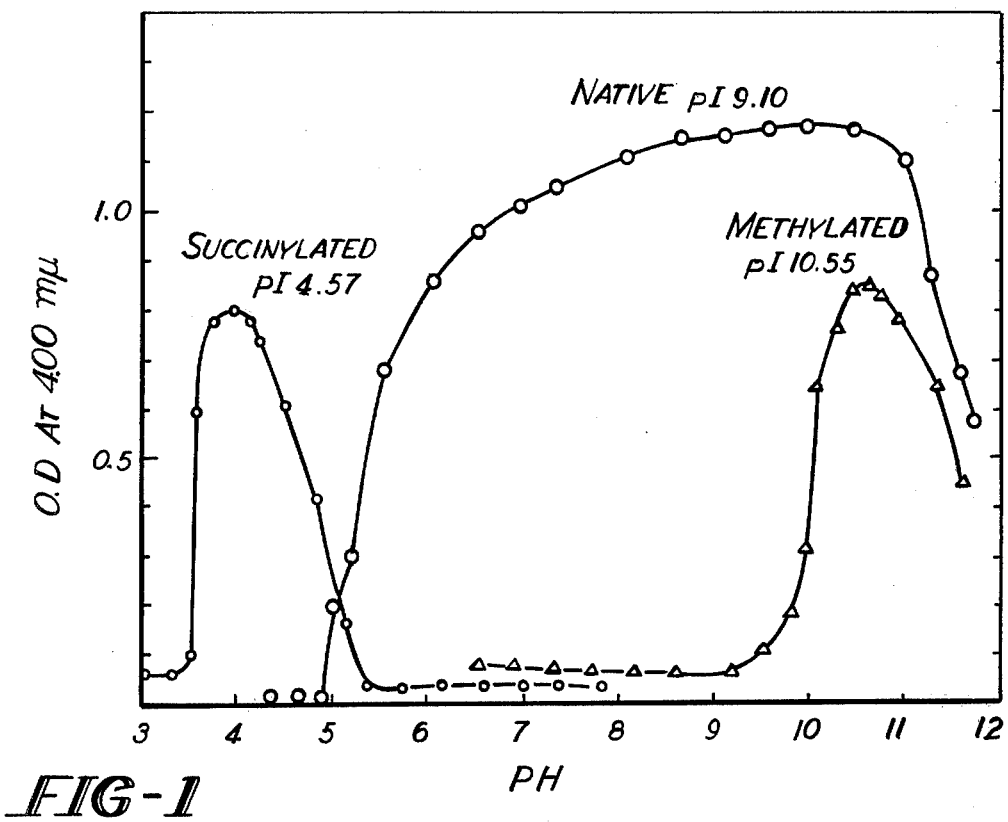

United States Patent [19]

Miyata et al.

[11] 4,164,559

[45] Aug. 14, 1979

[54] COLLAGEN DRUG DELIVERY DEVICE

[75] Inventors: Teruo Miyata, Tokyo, Japan; Albert L. Rubin; Kurt H. Stenzel, both of Englewood, N.J.; Michael W. Dunn, New Rochelle, N.Y.

[73] Assignee: Cornell Research Foundation, Inc., Ithaca, N.Y.

[21] Appl. No.: 835,302

[22] Filed: Sep. 21, 1977

[51] Int. Cl.² .................. A61K 9/00; A61K 47/00; A61K 37/12
[52] U.S. Cl. .................................. 424/14; 128/260; 424/19; 424/22; 424/28; 424/36; 424/359
[58] Field of Search .................. 128/260; 424/14–22, 424/28, 36, 359

[56] References Cited

FOREIGN PATENT DOCUMENTS 50-42025 4/1975 Japan ............................. 424/28

OTHER PUBLICATIONS

Stenzel et al., Ann. Rev. Biophysics and Bioengineering, vol. 3: 231–253, (1974), "Collagen as a Biomaterial".

Rubin et al., J. Clin. Pharmacol., vol. 13, (8/9):309–312, (1973), "Collagen as a Vehicle For Drug Delivery".

Chvapil et al., (1973), Int. Rev. Conn. Tiss. Res. 6:1–61, Medical and Surgical Applications of Collagen.

Green et al., (1953), Biochem. J. 54:181–187, "Acetylation of Collagen.

Olcott et al., (1961), Chem. Rev. 41:151–197, "Specific Group Reagents for Proteins".

Gustavson et al., (1961), Ark. Kemi 55:541–546, "Some Reactions of Succinylated Collagen".

*Primary Examiner*—Shep K. Rose
*Attorney, Agent, or Firm*—Edward J. Mahler

[57] ABSTRACT

Chemically-modified collagen membrane prepared at physiologic pH and soluble thereat provides a carrier for ophthalmic medication leaving no removable material after drug release.

9 Claims, 2 Drawing Figures (MEASURE OF SOLUBILITY)
FIBER FORMATIONS FOR NATIVE AND MODIFIED COLLAGENS

COLLAGEN DRUG DELIVERY DEVICE

This invention relates to a soluble collagen vehicle for drug delivery in ophthalmic practice. This invention also relates to the production of such vehicles preferably by using succinylated or methylated telopeptides-poor collagen which are soluble at physiologic pH and body temperature.

The main dosage forms of drug delivery to the eye are drops and ointment. For both forms, the duration of therapeutic effect is short-lived and repeated doses are required during the course of therapy because the drugs are rapidly washed out by reflex tear flow.

It is indispensable for the treatment of eye conditions requiring repeated application of drugs to develop a new drug delivery device which prolongs drug effect and attains precision in drug dose.

The chemistry, molecular structure and biochemical properties of collagen have been well established. An up-to-date review article by the current inventors (Annual Review of Biophysics and Bioengineering, Vol. 3, pp. 231-253, 1974) contains an excellent compilation of references on the subject.

Collagen is a major protein of connective tissue such as cornea, skin, etc., and can be solubilized and purified by the treatment with protelolytic enzymes (other than collagenase) such as pepsin. Solubilized collagen is telopeptides-poor, relatively inexpensive, not antigenic and useful as a biomedical material. Enzyme solubilized native collagen is soluble in acidic pH, insoluble at a physiologic pH and at body temperature.

In our previous studies, (Collagen as a Vehicle for Drug Delivery, J. Clin. Pharm. Vol. 13, No. 8, 309-312; August-September 1973) we reported results of drug delivery systems utilizing collagen films prepared from enzyme solubilized native collagen gels. Films incorporating the drug (e.g., pilocarpine) were inserted into the eye and when the drug became released therefrom the insoluble collagen film strip remained in the eye and had to be physically removed therefrom. The strip did not dissolve because the native collagen is insoluble at physiologic pH and at body temperature. The requirement of physical removal of the drug-depleted strip is undesirable, prone to non-professional and unsanitary removal techniques possibly resulting in damage or reinfection of the area. These disadvantages are overcome by the discovery entailed in this invention.

We have discovered that chemically modified collagen prepared and converted, for example, to gels and films, is in fact soluble under conditions of application for drug delivery, viz., soluble under physiologic pH and under normal body temperatures. By physiologic pH is meant a pH in a relatively narrow range as normally encountered in the fluids of the human body, i.e., a pH generally in the range of about 7.0 to about 7.5. For example, succinylation or methylation of collagen renders it soluble at a pH range of about 5.5 to 9.0 and particularly in the range of 7.0 to 7.5. FIG. 1 shows the solubility of various collagens as a function of pH. Solubility is determined by the extent of precipitation (formation of collagen fiber) as measured by optical density at 400mμ. Enzyme solubilized native collagen (without chemical modification, isoelectric point, pI 9.10), is soluble only in an acidic pH lower than 5. However, succinylated collagen (pI 4.57) is soluble at pH 5.5, thru the physiologic pH range and higher; while methylated collagen (pI 10.55) is soluble at pH 9, down through the physiologic range and lower to pH of 6.0. The solutions of native, succinylated and methylated collagens show high viscosity; for example, intrinsic viscosity is 12-15 dl/g which is about 25-30 times higher than gelatin solution (denatured collagen). In summary, optical densities of succinylated and methylated collagens are extremely low (less than 0.1) and constant in the neutral pH region. This means that these collagens are soluble and not precipitated.

The solubilization property of succinylated or methylated collagen at physiologic condition is therefore utilized to make a soluble device for drug delivery to the eye. The device containing the drug is gradually solubilized by the tear fluid, and the viscosity of tear film increases. Slow solubilization and viscosity increase are favorable for prolonging the effect of the drug and maintaining higher concentration level at the site of application.

Collagen has charge groups such as carboxyl and amino groups. The net charge of native collagen (without chemical modification) is almost zero at physiologic pH. However, succinylated collagen has a large negative net charge at physiologic pH and methylated collagen a large positive net charge. These negative or positive net charges are favorable to retaining oppositely charged drugs in the soluble device. The attractive interaction between drug and modified collagen prevents rapid release of the drug from the device.

The present invention is illustrated in detail in the following description:

Calfskin, steer hide, cow hide and pig skin collagens were used as a starting material. Dehaired and cleaned skin is solubilized with a proteolytic enzyme (pepsin, for example) and solubilized collagen is precipitated at pH 7 after in-activation of enzyme activity by caustic treatment at pH 10. The collagen is purified by repeating redissolution in acidic water (pH 2-4) and reprecipitation at pH 7.

Chemical modification of the amino groups may be performed by acylation with acetic anhydride or other anhydride such as succinic anhydride. Esterification of carboxyl groups may be carried out by standard reaction with acidified alcohol, preferably a water-soluble aliphatic alcohol such as methanol, ethanol, etc.

Methylated or succinylated collagen is dissolved in pH 3.0 dilute HCl solution at a concentration of 0.5%-2%. The drug is added to the collagen solution. Soluble collagen drug delivery device less than 20 mg can be conveniently placed in the inferior cul-de-sac of the eye; therefore an adequate mixing ratio of drug to collagen can be easily determined. For example, pilocarpine, dexamethazone and gentamicin are incorporated into collagen at a ratio of 1/30 to 1/2.5. Other drugs such as sulfapyridazine, atropine, dicain, neomycin, kanamycin, tetracycline and idoxuridine can also be incorporated into the soluble collagen device at a similar ratio.

After mixing of the drug into collagen, the pH is adjusted to 7.2 and de-airated under a vacuum for 10-30 minutes. The de-airated collagen-drug mixture is poured onto a plate of polymethylmethacrylate of 1 cm in depth and air dried to a membrane form. Dried collagen membrane containing the drug is cut into individual ovoid inserts of 5-20 mg in weight. To test the prolonging drug effect of the soluble succinylated collagen drug delivery device, the drug concentrations of tear film and in corneal and scleral tissues were measured. Similar results have been obtained for all drugs; therefore, only the result on gentamicin-soluble collagen device will be indicated as a representative example. For the comparison, other dosage forms such as eye drops, ointments and periocular injection were tested. Gentamicin-soluble collagen inserts were made of succinylated collagen, carrier gentamicin and $C^{14}$ gentamicin (radio active). A 10 mg ovoid insert contains $8.92 \times 10^5$ dpm of radioactive gentamicin and 1.1 mg carrier gentamicin. The drops and injection solutions and ointment were prepared to contain $8.92 \times 10^5$ dpm of radioactive gentamicin and 1.1 mg carrier gentamicin per one tenth ml.

Figure 2:
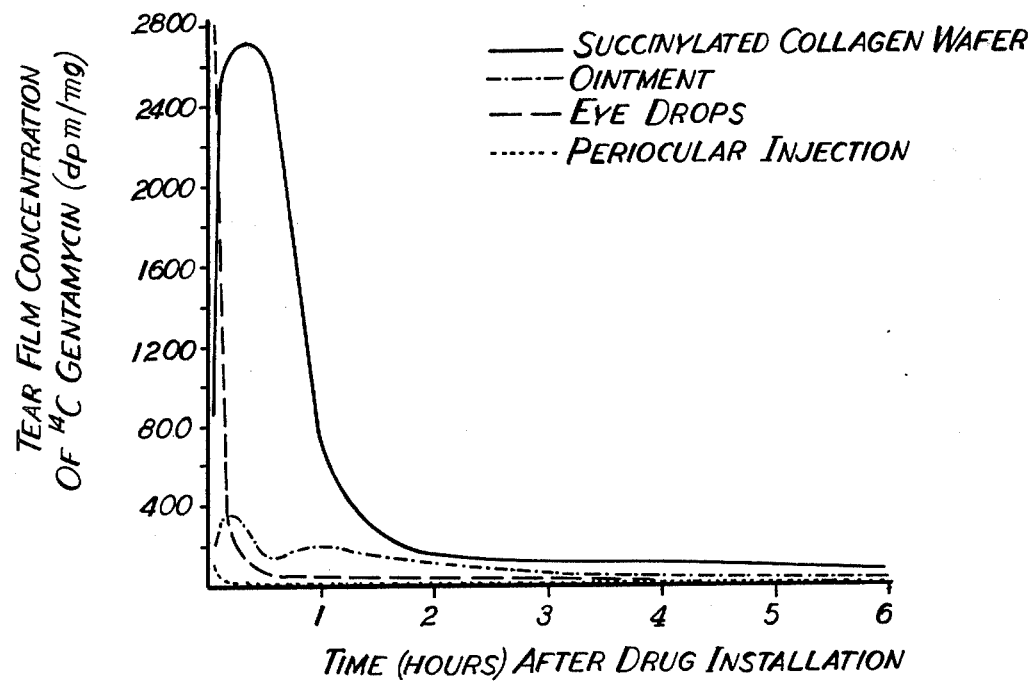

Ten mg of gentamicin-succinylated collagen insert, 0.1 ml of eye drop and ointment were placed in the inferior fornix of respective rabbit eye. 0.1 ml solution was subconjunctivally injected at 6:00 limbal position. The rabbits were made to blink every two minutes by flashing a strobe of light on each eye. Tear samples were taken after 5, 10, 20 and 30 minutes and 1, 2, 4 and 6 hours. Corneal tissues (3, 6, 9 and 12:00 positions and central) and scleral tissues (3, 6, 9, 12:00) were also taken after 1 and 3 hours. The radioactivity of the sample was measured. The results are indicated in FIG. 2 and Table 1.

Table 1
TISSUE CONCENTRATION OF $C^{14}$ GENTAMICIN
(Results in dpm/mg)

| Route of Administration | Sample | | | | | | | | |
|---|---|---|---|---|---|---|---|---|---|
| | Sclera | | | | Cornea | | | | |
| 1 Hour | 12 | 9 | 3 | 6 | 12 | 9 | 3 | 6 | C |
| Succinylated Collagen wafer | 65 | 45 | 67 | 66 | 30 | 20 | 58 | 35 | 21 |
| Periocular injection | 33 | 35 | 48 | 121 | 12 | 11 | 13 | 18 | 5 |
| Ointment | 19 | 25 | 30 | 32 | 14 | 17 | 16 | 16 | 15 |
| Drops | 18 | 14 | 14 | 12 | 10 | 9 | 12 | 12 | 6 |
| 3 Hour | | | | | | | | | |
| Succinylated Collagen wafer | 18 | 33 | 44 | 28 | 9 | 12 | 14 | 11 | 15 |
| Periocular injection | 7 | 36 | 28 | 27 | 4 | 5 | 5 | 4 | 4 |
| Ointment | 5 | 5 | 6 | 14 | 7 | 4 | 9 | 2 | 3 |
| Drops | 5 | 6 | 5 | 7 | 4 | 4 | 5 | 3 | 4 |

Soluble succinylated collagen inserts showed the highest and most sustained concentration of radioactivity with levels dropping off only after two hours for tear film. Also the concentration in the tissues was highest for such soluble collagen insert. These results indicate modified collagen soluble at physiologic pH is an effective drug delivery device for delivering medication and prolonging the therapeutic effect in the eye.

The present invention may be further understood from the following examples:

EXAMPLE 1

Fresh calf skin (about 5 kg) was dehaired, cleaned by shaving and cut into small pieces. The skin was solubilized in 10 liters of water (pH 2.5 HCl) by addition of 1 g of pepsin (approximate ratio of enzyme to collagen is 1/400) and kept at 20° C. for five days with intermittent stirring. The resulting viscous solubilized collagen was filtered through cheesecloth, its pH adjusted to 10 by NaOH and allowed to stand for 24 hours at 4° C. to inactivate the pepsin. The pH of collagen was then adjusted to 7 to 8 (HCl) and collagen precipitate was collected by centrifuging. Collagen was further purified by repeating redissolution in acidic aqueous solution and reprecipitation at pH 7. Succinylation of collagen was accomplished by the following procedure: Five grams of solubilized collagen was solubilized in 2 liters of acidified water (pH 3.0 HCl) and the pH adjusted to 9.0 by NaOH. Acetone solution (100 ml) containing 2g succinic anhydride was gradually added to the collagen suspension. During the addition of succinic anhydride the pH of collagen suspension was maintained at about 9.0 by NaOH. Succinylated collagen was precipitated by acidification to about pH 4.2, washed repeatedly with water and freeze-dried.

Three grams of succinylated collagen were dissolved in 200 ml of acidified water (pH 3, HCl) and 600 mg of pilocarpine HCl was mixed with the collagen. The pH was adjusted to 7.0 by NaOH and de-airation was performed in a vacuum for 30 minutes. It was poured onto a polymethylmethacrylate plate with a depth of 1 cm and air-dried. Dried membrane was cut into individual ovoid wafers of 10 mg which contained 7.5 mg collagen, 1.5 mg pilocarpine and 1.0 mg moisture.

This pilocarpine-succinylated collagen drug delivery insert showed excellent prolonged therapeutic effect, lowering the ocular pressure during more than 24 hours with one dosage. The insert became completely solubilized and no residue was observed.

EXAMPLE 2

Enzyme solubilized collagen prepared by the procedure of Example 1 was methylated by the following method: Collagen fiber precipitated at pH 7 was collected by centrifugation and freeze-dried. Ten grams of freeze-dried collagen was immersed in 2 liters of dehydrated methanol containing 0.1N HCl for 7 days at room temperature in a tightly sealed vessel. Dehydration of methanol containing HCl prior to addition of collagen was carried out by intermittent stirring with excess anhydrous sodium sulfate. After methylation, the collagen was dried in a vacuum and redissolved in aqueous HCl solution (pH 3) at a concentration of 1.5%.

To 200 ml of 1.5% methylated collagen solution was added and mixed 300 mg of dexamethazone. The pH of the methylated collagen was adjusted to 7.0 and the gel was de-airated in a vacuum of 10–30 minutes. The collagen gel was poured onto a plate of polymethylmethacrylate with a depth of 1 cm and air-dried. Dried membrane was cut into an individual ovoid insert of 10 mg. Ten mg of each insert contained 8.2 mg methylated collagen, 0.80 mg dexamethazone and 1.0 mg moisture.

This dexamethazone-methylated collagen drug delivery insert showed excellent prolonged therapeutic effect by one insertion in the inferior cul-de-sac. The insert was completely soluble and no residue was observed.

EXAMPLE 3

Succinylated collagen was prepared by the method of Example 1. Two grams of succinylated collagen was dissolved in 200 ml of pH 3 water (HCl) and 400 mg of gentamicin was mixed to collagen solution. Collagen solution was poured onto a plate of polymethylmethacrylate with a depth of 1 cm after it was de-aired in a vacuum for 10 minutes and air-dried. The dried membrane was cut into individual ovoid inserts of 10 mg in weight which contained 7.5 mg succinylated collagen, 1.52 mg gentamicin and 0.98 mg moisture.

This gentamicin-succinylated collagen drug delivery insert showed excellent prolonged therapeutic effect by one insertion in the inferior fornix of the eye. The collagen insert was completely soluble and no residue was observed.

Having described the invention in the above detail, what is claimed is:

1. An ophthalmic drug delivery system comprising (a) an enzyme-extracted, chemically-modified collagen thin membrane carrier selected from the group consisting of esterified collagen and acylated collagen and having a pH in the range of 5.5-9.0 whereby the carrier is soluable in the tear fluid under physiologic conditions, and (b) an ophthalmically active drug incorporated into said carrier.

2. The system of claim 1 in which the carrier is esterified collagen.

3. The system of claim 1 in which the carrier is acylated collagen.

4. The system of claim 1 in which the drug is at least one drug selected from the group consisting of pilocarpine, dexamethazone, gentamycin, sulfapyridazine, atropine, dicain, neomycin, kanamycin, tetracycline and idoxuridine.

5. The system of claim 2 in which the carrier is methylated collagen.

6. The system of claim 3 in which the carrier is succinylated collagen.

7. A method for preparing an ophthalmic drug delivery device soluable at physiologic pH and at body temperature which comprises forming a gel from enzyme-extracted, chemically-modified collagen selected from the group consisting of esterified collagen and acylated collagen, adding an ophthalmically-active drug to the gel, adjusting the pH of the gel to a range of 5.5 to 9.0, de-airating and drying the drug-containing gel to form a thin membrane thereof, and shaping the membrane to ocular insert form.

8. The method of claim 7 in which the collagen is succinylated collagen and in which the drug is pilocarpine.

9. The method of claim 7 in which the collagen is methylated collagen and in which the drug is dexamethazone.

* * * * *